United States Patent
Abbasi et al.

(10) Patent No.: US 6,780,378 B2
(45) Date of Patent: Aug. 24, 2004

(54) METHOD FOR MEASURING CONCENTRATIONS OF GASES AND VAPORS USING CONTROLLED FLAMES

(75) Inventors: Hamid A. Abbasi, Naperville, IL (US); David M. Rue, Chicago, IL (US)

(73) Assignee: Gas Technology Institute, Des Plaines, IL (US)

( * ) Notice: Subject to any disclaimer, the term of this patent is extended or adjusted under 35 U.S.C. 154(b) by 403 days.

(21) Appl. No.: 09/894,066

(22) Filed: Jun. 28, 2001

(65) Prior Publication Data

US 2003/0003590 A1 Jan. 2, 2003

(51) Int. Cl.[7] .................. G01N 31/12; G01N 21/72; F23N 5/08
(52) U.S. Cl. .................. 422/78; 422/54; 422/80; 431/12; 431/76; 431/79; 436/116; 436/117; 436/118; 436/133; 436/134; 436/136; 436/137; 436/143; 436/155; 436/160; 436/171
(58) Field of Search .................. 436/136–137, 436/143, 155, 160, 171, 116–118, 133–134; 422/54, 78, 80, 91; 431/12, 76, 79, 353

(56) References Cited

U.S. PATENT DOCUMENTS

| | | | |
|---|---|---|---|
| 2,603,085 A | * | 7/1952 | Cannon, Jr. .................. 73/23.31 |
| 2,885,926 A | | 5/1959 | Molloy |
| 3,592,608 A | * | 7/1971 | White .................. 422/78 |
| 3,609,042 A | | 9/1971 | Yasuda et al. |
| 3,917,405 A | | 11/1975 | Hartmann et al. |
| 3,955,914 A | * | 5/1976 | DeLew .................. 431/353 |
| 4,097,239 A | * | 6/1978 | Patterson .................. 436/106 |
| 4,370,060 A | | 1/1983 | Murase et al. |
| 4,429,047 A | | 1/1984 | Jastrzebski et al. |
| 4,447,204 A | * | 5/1984 | Isenberg .................. 431/76 |
| 4,466,943 A | | 8/1984 | Murase et al. |
| 4,801,209 A | | 1/1989 | Wadlow |
| 5,708,507 A | | 1/1998 | Wright, Jr. et al. |
| 5,741,711 A | | 4/1998 | Amirav et al. |
| 6,091,504 A | | 7/2000 | Walker et al. |
| 6,247,918 B1 | * | 6/2001 | Forbes et al. .................. 431/12 |

OTHER PUBLICATIONS

Bruinsma, O. S. L. et al, Fuel 1985, 64), 1468–1475.*
Cheskis, S. et al, SPIE 1994, 2124, 145–151.*
Von Drasek, W. et al, SPIE 1999, 3535, 215–225.*

* cited by examiner

*Primary Examiner*—Arlen Soderquist
(74) *Attorney, Agent, or Firm*—Mark E. Fejer

(57) ABSTRACT

A method and apparatus for measuring the concentration of at least one gaseous component and/or vaporous component of a gaseous mixture in which a controlled sensor flame is introduced into the gaseous mixture and at least one narrow spectral band in the controlled sensor flame is optically measured. The concentration of the gaseous component using a result obtained from the optical measuring of the at least one narrow spectral band is then calculated. The method of this invention is particularly suitable for substantially real-time control of combustion processes.

3 Claims, 3 Drawing Sheets

METHOD FOR MEASURING CONCENTRATIONS OF GASES AND VAPORS USING CONTROLLED FLAMES

BACKGROUND OF THE INVENTION

1. Field of the Invention

This invention relates to a method for measuring the concentration of gases and vapors in a gaseous mixture. More particularly, this invention relates to a method for measuring the concentration of oxygen in a gaseous mixture. This invention is particularly useful for measuring oxygen concentration in hot, dirty exhaust gases from combustion processes. In addition, this invention provides a means for real-time control of combustion processes based upon the concentration of oxygen or combustion-derived gases or other gases and vapors in the exhaust gases of the combustion processes.

2. Description of Prior Art

There are three basic methods for measuring the concentration of oxygen in a gas mixture in commercial use. However, due to their cost, the inherent time delay in obtaining the results and their unreliability in harsh industrial environments, which typically include a combination of heat, corrosive gases, dust and the like, none of these methods is rugged, low-cost or reliable enough to provide input to combustion control systems.

Paramagnetic oxygen analyzers are commonly used in continuous emissions monitoring systems. These analyzers measure the paramagnetic susceptibility of the sample gas by means of a magnetic-dynamic type measuring cell. While this technique is accurate and reliable, disadvantages of these instruments include the need for regular calibration and a response time that is too slow for control applications. In addition, the cell must be maintained at a constant temperature, for example 50° C., and the gas must be dry. In practice, exhaust gas samples must be cooled and dried before being sent to the analyzer, which results in significant time delays.

Commercially available electrochemical analyzers capable of directly measuring oxygen concentrations in hot exhaust gases utilize zirconium dioxide ($ZrO_2$) as a solid electrolyte and platinum, NiCr and/or other compounds, as electrode materials. The anode is exposed to a reference gas while the cathode is exposed to the sampled gas stream. Zirconia is an ionic conductor at temperatures above 600° C. As a result, variation in the electrochemical potential of the cell reflects variation of the oxygen content of the sampled gas. While response time is rapid, these analyzers have several disadvantages including high labor maintenance costs, the use of expensive materials required to make the sensors, and a short service life of only six to 12 months in harsh environments.

A serious disadvantage of traditional continuous emissions monitors is a substantial time delay between the moment of combustion and when the results of the analysis are complete because the sample must be extracted from the flue gas stream, dried and finally analyzed. This makes the implementation of continuous emissions monitors for burner control very difficult. Optical sensors are capable of overcoming this problem. Narrow-band optical detection of intermediate species within the burner flame overcomes this time lag. In flame analyzers, different wavelength radiation sensors, filters and data acquisition and processing systems are combined to measure concentrations of a number of radicals formed during the combustion process including OH, CO, and CH. This information is used to determine the air/fuel ratio and the presence of soot. See, for example, U.S. Pat. No. 5,741,711, which teaches a method and apparatus for analyzing a sample by introducing the sample into a combustible mixture, igniting the combustible mixture to produce a flame, and detecting a characteristic of the resulting flame to determine the identity and/or concentration of one or more chemical substances in the sample, wherein the combustible gas mixture is generated by water electrolysis. The apparatus includes an inlet for introducing combustible gases, a feeder for introducing the sample into the combustible gases, an ignitor for igniting the combustible gases to produce a flame, a detector for detecting a characteristic of the resulting flame for determining the identity and/or concentration of one or more chemical substances in the sample, and a water electrolyser for generating combustible gases and for directing the gases to the inlet. This technique has a number of serious problems and limitations in industrial practice. System calibration is difficult, and there is typically strong interference from refractory or wall radiation. Flame turbulence requires sophisticated data processing to separate signals from noise. In addition, the radiation spectrum coming from real, industrial scale, flames often is estimated as black body radiation spectrum making separate radiation intensity measurements associated with detectable radicals difficult.

U.S. Pat. No. 5,708,507 teaches a method and apparatus for temperature resolved molecular emission spectroscopy of solid, liquid or gaseous materials in which a sample is vaporized and decomposed, and the vaporous sample is then transported into a combustion flame. A spectrum of intensity in the optical emission from the flame at a selected wavelength versus temperature of the sample defines molecular peaks which are characteristic of the sample material and allows both qualitative and quantitative analysis of the sample. See also U.S. Pat. No. 3,917,405 which teaches the use of a flame photometric detector for analysis of a sample burned in a flame and U.S. Pat. No. 3,609,042 which teaches an optical measuring apparatus for sampling material in which the samples are introduced into a flame and light beams which pass through the flame are detected by a detector which, in turn, produces electric signals corresponding to the concentrations of the samples within the flame.

Another method and apparatus for determining the concentration of an analyte such as oxygen in an unknown gas sample is taught by U.S. Pat. No. 6,091,504 in which a vertical cavity surface emitting laser is used as a variable wavelength light source which is "swept" through a wavelength range by varying the drive signal applied thereto. The variable wavelength light source is repeatedly "swept" through a range of frequencies determined by the drive signal, and the absorption is measured by the detector.

Notwithstanding the number of known methods and devices for analyzing the content of a gaseous mixture, none of them provide real-time analysis whereby the results may be employed to control an application, such as a combustion process. In addition, known methods and devices do not simultaneously measure oxygen concentration and the concentrations of other gases, including CO, total hydrocarbons, $NO_x$ and the like in static and flowing gases, including harsh industrial exhaust gas streams.

SUMMARY OF THE INVENTION

Accordingly, it is one object of this invention to provide a method and apparatus for measuring the oxygen concentration of gaseous mixtures in harsh industrial environments.

It is another object of this invention to provide a method and apparatus for measuring the concentrations of oxygen and other gaseous and vaporous components of a gaseous mixture which is not affected by the presence of contaminants including dust, halides, $NO_x$ and $SO_x$.

It is yet another object of this invention to provide a method and apparatus for simultaneous measurement of $O_2$, CO, total hydrocarbons and other gaseous and vaporous components of flue gases.

It is yet a further object of this invention to provide a method and apparatus for measuring the oxygen concentration of a gaseous mixture which does not require frequent calibration.

These and other objects of this invention are addressed by a method for measuring the concentration of at least one gaseous and/or vaporous component of a gaseous mixture comprising the steps of introducing a controlled sensor flame into the gaseous mixture, optically measuring at least one narrow spectral band in the controlled sensor flame, and calculating a concentration of the gaseous and/or vaporous component using the result obtained from the optical measuring of the at least one narrow spectral band, the narrow spectral band being less than 20 nanometers, and preferably less than 10 nanometers, in width. Although similar to known methods for measuring the gaseous content of a gaseous sample, the method of this invention is distinguishable in that it does not involve or require the introduction of the sample directly into the flame. For measuring the oxygen concentration of flue gases, the observed oxygen concentration data is acquired sufficiently close to the flame, soon enough after the combustion process, and reliably enough to be used by a combustion control system to optimize combustion efficiency and minimize emissions in substantially real time. Conventional oxygen sensors and methods for determining oxygen concentration in a gaseous stream do not have these capabilities.

Advantages of using controlled flames as a means for monitoring combustion emissions include the ability to operate reliably and continuously for extended periods of time in harsh industrial environments and simultaneous measurement of oxygen, carbon monoxide, total hydrocarbons and even $NO_x$. In addition, the presence of contaminants including dust, halides, $NO_x$ and $SO_x$ does not impair operation and the equipment required to carry out the method is simple, inexpensive and does not require continuous calibration. Yet a further advantage of the method and apparatus of this invention is the range of gas mixtures that can be analyzed for oxygen concentration. Measuring the oxygen concentration of "dirty", hot gases such as exhaust gases from industrial combustion processes using conventional means is difficult. This invention provides a means for determining oxygen concentrations of these difficult gas mixtures and for measuring oxygen concentration in other static and flowing gas mixtures at less stringent conditions.

Finally, this invention offers significant advantages to the operators of industrial combustion processes because the oxygen concentration data from the dirty, hot exhaust gases immediately downstream of a furnace provides direct information regarding the combustion process. The data available from conventional systems only provide indirect information about the combustion process. The immediate availability of the oxygen concentration in the dirty, hot exhaust gases enables the combustion process control system and operators to optimize the combustion process in real time.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

The concentrations of oxygen and other gases and vapors in a gas mixture in accordance with the method of this invention are determined by making optical measurements of narrow spectral bands in a controlled sensor flame placed in the gas mixture. As used herein, the term "narrow spectral band" refers to light wavelength ranges of less than about 20 nanometers, and preferably less than 10 nanometers, in width. The observed optical bands correspond to excited energy levels of various radical species including, but not limited to, O—H, C—H, and C—C, that are located in the ultraviolet and visible regions of the spectrum. Measurements of other characteristics of the controlled sensor flame, including temperature near or in the flame, flame length, flame shape, etc. may also be made along with the intensities of narrow spectral band optical readings to assist in determining oxygen concentrations. The information collected from the controlled sensor flame is input to software that calculates the oxygen concentration in the gas around the controlled sensor flame. The sensor flame must be maintained at known "controlled" conditions at all times. To achieve this result, the controlled sensor flame may be generated in several specific ways. The software correlates digitized narrow spectral band intensity data and other data, including temperature, flame shape and flame length with the concentration of oxygen and other gaseous or vaporous components.

In accordance with one embodiment of this invention, the controlled sensor flame is generated by burning a hydrocarbon fuel, preferably a gaseous fuel, such as methane or natural gas, with an oxidant containing a known amount of oxygen between 21 and 100 volume percent. The fuel and oxidant rates and volumetric ratio are precisely controlled, as is the flame velocity. In accordance with another embodiment of this invention, the controlled sensor flame is generated by introducing a precisely controlled flow rate of a gaseous fuel, such as methane or natural gas, into a hot gas stream. The fuel velocity is precisely controlled. The hot gas stream into which the gaseous fuel is introduced must be sufficiently high in temperature and contain sufficient oxygen to establish and maintain a stable flame. In accordance with yet another embodiment of this invention, the controlled sensor flame is generated either in a gas mixture with an unknown oxygen volume fraction or in a separate chamber containing a known gas composition at a known temperature. In accordance with this embodiment, the gaseous fuel is burned with a known amount of oxidant containing a known portion of gas from the unknown gas mixture and a known amount of oxidant containing from 21 to 100 volume percent oxygen. The fuel and oxidant rates and the volumetric ratio are precisely controlled, as is flame velocity.

Figure 1:
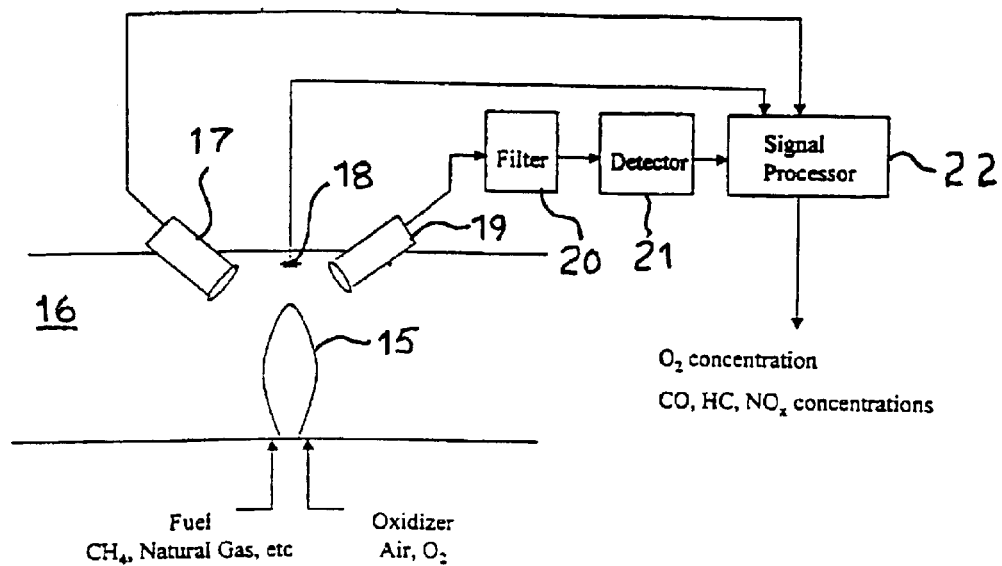
FIG. 1 is a schematic diagram of a system for carrying out the method of this invention.

As previously stated, the method of this invention can be employed to measure gaseous concentration in a static or flowing gas mixture in several different configurations. FIG. 1 is a schematic diagram of a system for carrying out the method of this invention and represents one of the simpler methods of using a controlled sensor flame. In accordance with the embodiment shown in FIG. 1, the controlled sensor flame is observed while inside the static or flowing gas mixture of concern. This embodiment also provides the broadest range of application to obtain oxygen concentration data or to acquire near real-time oxygen concentration data that can be sent to a combustion control system. The system as shown is suitable for measuring oxygen concentration in a hot, flowing exhaust gas. The oxygen concentration data is available on a continuous basis for use by a combustion control system.

As shown in FIG. 1, the system comprises a controlled sensor flame 15 disposed in a static or flowing gas mixture 16, a flame shape and/or length detector 17, temperature measurement means 18 for measuring the temperature of the static or flowing gas mixture 16, optical sensor 19, the output of which is passed through narrow band spectral filter 20 and detector 21, and signal processor 22 which analyzes the signals from flame shape and/or length detector 17, temperature measurement means 18 and optical sensor 19 to arrive at the concentration of the desired gas within the gas mixture.

In operation, optical sensor 19 acquires data on concentrations of specific radicals at one or more precise locations in sensor flame 15. This is achieved by measuring the intensities from the controlled sensor flame 15 over a narrow band of wavelengths. Light intensity from only one, or at most two, wavelengths needs to be monitored. This allows for much simpler and less costly approaches to be used for measuring specific wavelengths. Several techniques can be used, but the primary options are the use of narrow bandwidth filters 20, as shown in FIG. 1, or the use of controlled diffraction gratings in combination with commercially available, inexpensive radiation detectors. This equipment is much less expensive and much more robust than spectrophotometers which are not normally used in harsh industrial environments.

Because the concentrations at one or more locations in sensor flame 15 can be influenced by flame length or shape and temperature of the surrounding gas, data on the flame dimensions is collected by flame shape and/or length detector 17 and gas mixture temperature is collected by temperature measurement means 18. Any means suitable for measuring the temperature of the gas mixture known to those skilled in the art may be employed. The flame dimension and/or gas temperature data are then combined with the optical data generated by optical sensor 19 to determine the concentration of the desired gas in the gas mixture. Signal processor 22 is preferably a microprocessor-based module which determines the gas concentration from the flame and gas mixture data using known correlations.

The method of this invention is particularly suitable for use in measuring oxygen concentrations in gaseous mixtures such as hot flue gases. The measurement of oxygen concentrations in a gas mixture by observing narrow-band optical characteristics of a controlled sensor flame in that gas mixture in accordance with the method of this invention affords substantial benefits over conventional oxygen measurement methods. The method provides the potential for measuring oxygen concentration while simultaneously measuring the concentrations of other gas species, including carbon monoxide, total hydrocarbons, and $NO_x$, in any static or flowing gas, including harsh industrial exhaust gas streams. Sensors suitable for use in the method of this invention are simple, reliable and inexpensive enough for cost-effective use by industry. In addition, the observed oxygen concentration data is acquired close enough to the flame, soon enough after the combustion process, and reliably enough to be used by the combustion control system to optimize combustion efficiency and minimize emissions. Yet a further advantage of the method of this invention is the fact that the presence of contaminants including dust, halides, $NO_x$ and $SO_x$ does not impair operation.

To test the controlled flame sensor used in the method of this invention, we placed a controlled flame with fixed gas and air flow rates and velocities in the exhaust duct of a high temperature furnace. The main furnace burner was then operated over a wide range of conditions to produce exhaust gases with oxygen concentrations of 0 to about 5 volume percent at temperatures up to about 2000° F. The controlled flame in the exhaust duct was viewed through a sight glass using a radiation detector (a CCD camera) and a series of narrow bandwidth, near-UV and visible light filters.

Figure 2A:
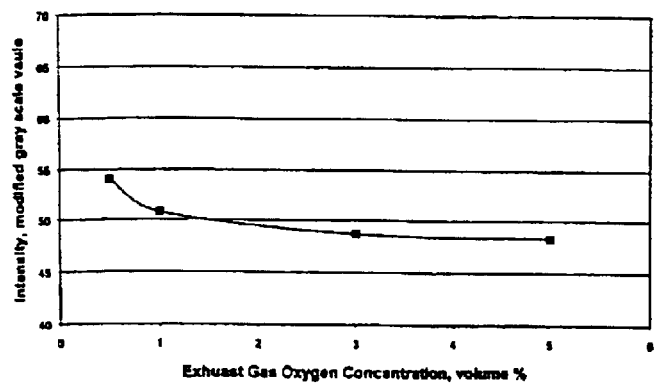
FIGS. 2a and 2b are diagrams showing the correlation between exhaust gas concentration and gray scale intensity measured by a CCD camera at 1975° F. and 1680° F., respectively.
Figure 2B:
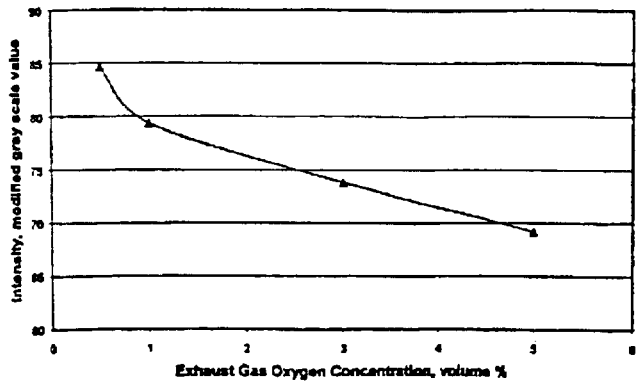

FIGS. 2a and 2b demonstrate that there is a strong correlation between exhaust gas oxygen concentration and gray scale intensity measured by the CCD camera. Intensities are affected by oxygen concentration and temperature. The curves shown in FIGS. 2a and 2b are actual gray scale intensity measurements at 1975° F. and 1680° F., respectively, for a specific 30 nm wavelength bandwidth. Data collected over an even wider temperature range consistently shows a one-to-one mapping with oxygen concentration.

Figure 3:
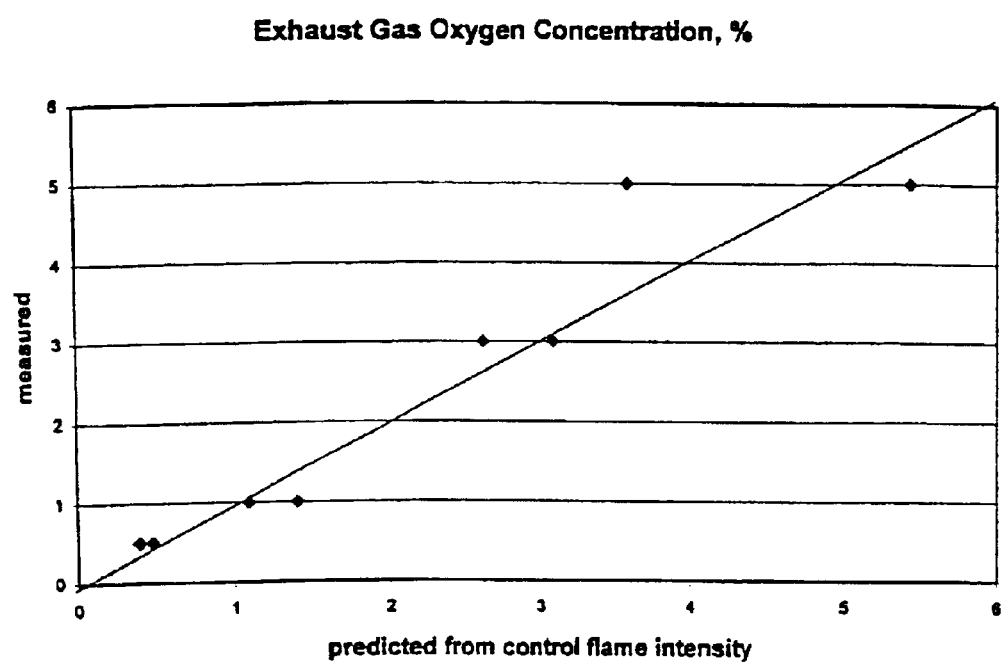
FIG. 3 is a diagram showing the accuracy and precision of oxygen concentration measurements made in accordance with the method of this invention.

Gray-scale intensity was used to correlate predicted and measured exhaust gas concentrations from about 0 to about 5 volume percent and at temperatures up to about 2000° F. Straightforward regression, as shown in FIG. 3, confirms the ability to predict oxygen concentrations over a wide range of exhaust gas conditions.

Figure 4:
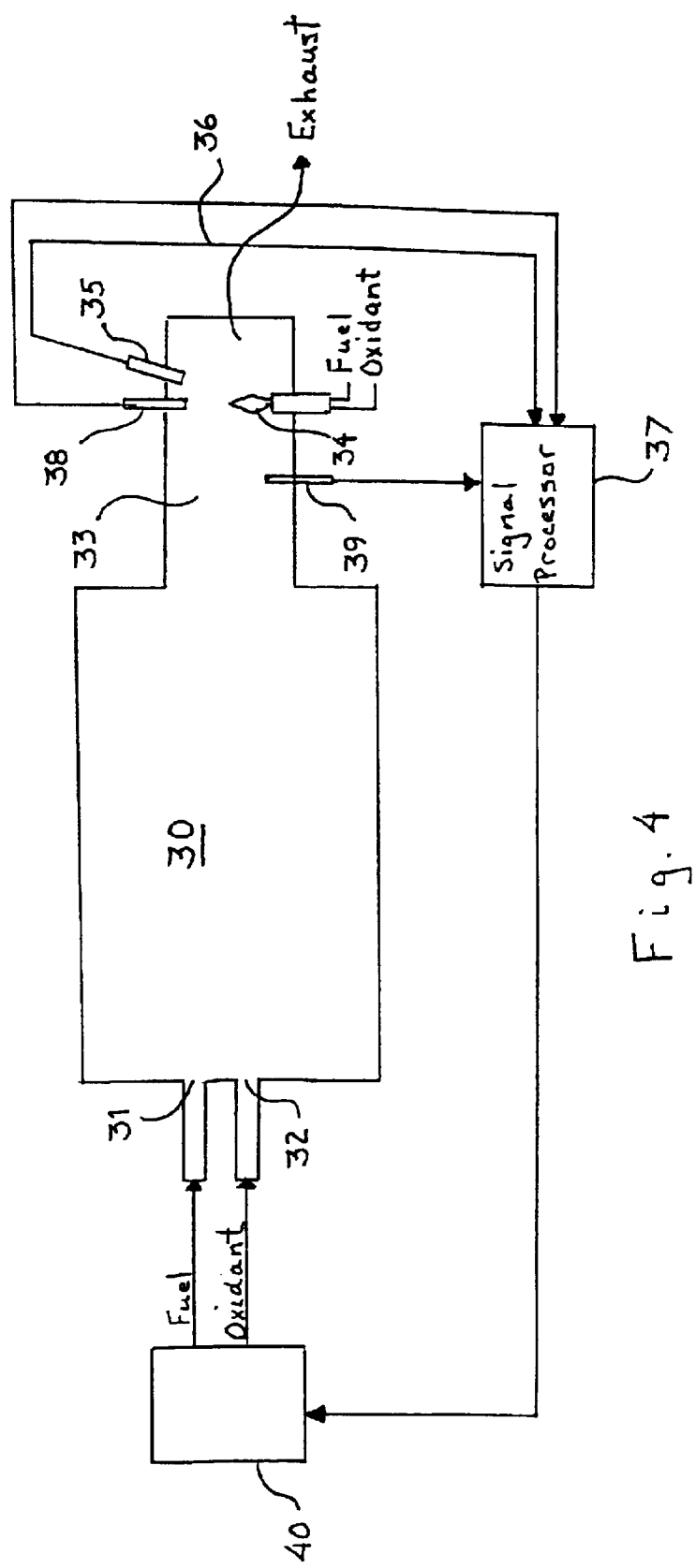
FIG. 4 is a schematic diagram of a combustion system employing the method of this invention.

FIG. 4 shows a combustion system suitable for employing the method of this invention. The system comprises a combustion chamber 30 having means for introducing a fuel and oxidant into said combustion chamber. As shown in FIG. 4, said means for introducing fuel and oxidant into the combustion chamber comprise separate fuel and oxidant inlets 31 and 32. It will, however, be apparent to those skilled in the art that the fuel and oxidant may be introduced into combustion chamber 30 through a common inlet, either separately or as a mixture. Exhaust conduit 33 in fluid communication with combustion chamber 30 conveys products of combustion resulting from combustion of the fuel and oxidant away from combustion chamber 30. Disposed within exhaust conduit 33 is a controlled sensor flame 34. Optical sensor 35 is disposed proximate exhaust conduit 33 and adapted to measure at least one narrow spectral band in and/or proximate the controlled sensor flame. Optical sensor 35 comprises a signal output 36 operably connected to signal processor 37. Signal processor 37, which, based upon a signal received from optical sensor 35, controls the flow of fuel and oxidant into combustion chamber 30, is operably connected to control means 40 for controlling the introduction of fuel and oxidant into combustion chamber 30. In accordance with one preferred embodiment of this invention, the apparatus further comprises a flame shape sensor 38 adapted to determine at least one dimension of controlled sensor flame 34 operably connected to signal processor 37. In accordance with yet a further embodiment of this invention, the apparatus comprises temperature means 39 for measuring a temperature of the products of combustion proximate controlled sensor flame 34 operably connected to signal processor 37. Any means for measuring the temperature of the products of combustion known to those skilled in the art which provides an output signal for introduction into signal processor 37 may be employed.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. An apparatus comprising:
    a combustion chamber having means for introducing a fuel and oxidant into said combustion chamber and an exhaust conduit suitable for conveying products of combustion from said combustion chamber in fluid communication with said combustion chamber;
    control means for controlling a flow of said fuel and oxidant into said combustion chamber;
    a controlled sensor flame disposed in said exhaust conduit;
    an optical sensor adapted to measure at least one narrow spectral band at least one of in and around said controlled sensor flame, said optical sensor having a signal output;
    signal processing means for converting a signal generated by said optical sensor to a gas concentration of at least one of a gas and a vapor disposed in said products of combustion operably connected to said signal output; and
    a flame shape sensor adapted to determine at least one dimension of said controlled sensor flame operably connected to said signal processing means.

2. An apparatus in accordance with claim 1, wherein said signal processing means is operably connected to said control means and controls said flow of fuel and oxidant into said combustion chamber based upon said signal generated by said optical sensor.

3. An apparatus in accordance with claim 1 further comprising temperature means for measuring a temperature of said products of combustion proximate said controlled sensor flame operably connected to said signal processing means.

* * * * *